(12) United States Patent
Chen et al.

(10) Patent No.: US 9,877,662 B2
(45) Date of Patent: Jan. 30, 2018

(54) VESSEL SENSING DEVICE WITH AUTOMATIC AMENDMENT FUNCTION

(71) Applicant: PixArt Imaging Inc., Hsin-Chu (TW)

(72) Inventors: Peng-Sheng Chen, Hsin-Chu (TW); Hsiang-Wei Hwang, Hsin-Chu (TW); Jui-Te Chiu, Hsin-Chu (TW)

(73) Assignee: PixArt Imaging Inc., Hsin-Chu (TW)

( * ) Notice: Subject to any disclaimer, the term of this patent is extended or adjusted under 35 U.S.C. 154(b) by 210 days.

(21) Appl. No.: 14/746,807

(22) Filed: Jun. 22, 2015

(65) Prior Publication Data

US 2016/0120463 A1 May 5, 2016

(30) Foreign Application Priority Data

Nov. 3, 2014 (TW) .............................. 103138082 A

(51) Int. Cl.
*A61B 5/02* (2006.01)
*A61B 5/024* (2006.01)
*A61B 5/08* (2006.01)
*A61B 5/00* (2006.01)

(52) U.S. Cl.
CPC .......... *A61B 5/02438* (2013.01); *A61B 5/082* (2013.01); *A61B 5/681* (2013.01)

(58) Field of Classification Search
CPC .............. A61B 5/0261; A61B 5/02416; A61B 5/02427; A61B 5/02433; A61B 5/02438
See application file for complete search history.

(56) References Cited

U.S. PATENT DOCUMENTS

2014/0316305 A1* 10/2014 Venkatraman ........ A61B 5/1112
600/595

* cited by examiner

*Primary Examiner* — Michael Kahelin
(74) *Attorney, Agent, or Firm* — Winston Hsu

(57) ABSTRACT

A vessel sensing device with automatic amendment function includes an analog processing circuit, a signal generating circuit and a DC voltage detecting circuit. The analog processing circuit includes an optical sensing module. An optical sensor of the optical sensing module generates an analog signal with a skin characteristic signal and a vessel characteristic signal according to an optical reflecting signal. The skin characteristic signal and the vessel characteristic signal respectively correspond to a skin feature and a vessel feature of the user. The signal generating circuit is coupled to the analog processing circuit to transform the analog signal into a compensation signal. The DC voltage detecting circuit is coupled to the signal generating circuit and adapted to compensate the analog processing circuit according to the compensation signal, so as to decrease the skin characteristic signal within the analog signal.

10 Claims, 3 Drawing Sheets

VESSEL SENSING DEVICE WITH AUTOMATIC AMENDMENT FUNCTION

BACKGROUND OF THE INVENTION

1. Field of the Invention

The present invention relates to a vessel sensing device, and more particularly, to a vessel sensing device with automatic amendment function by deducting color noise of the skin surface texture.

2. Description of the Prior Art

With the advanced technology, the wearable device has property of convenient portability and handy design, and the user can use the wearable device for physiological monitoring while in the gym or the ordinary life. The wearable device is worn on the skin of human body, such as the wrist. The wearable device monitors physical parameters and/or mental parameters by the biological feature sensor. The biological feature sensor can be a vessel sensor. The wearable device utilizes the vessel sensor to sense heart rhythm and breath rhythm of the user and display sensed information on the screen. However, the vessel is located under the skin texture, and precision of the conventional vessel sensor is decreased by skin color, skin roughness and/or fat thickness, so the conventional vessel sensor cannot effectively distinguish difference of the skin texture characteristic and the vessel characteristic cannot be accurately filtered for recognition.

SUMMARY OF THE INVENTION

The present invention provides a vessel sensing device with automatic amendment function by deducting color noise of the skin surface texture for solving above drawbacks.

According to the claimed invention, a vessel sensing device with automatic amendment function includes an analog processing circuit, a signal generating circuit and a direct current (DC) voltage detecting circuit. The analog processing circuit includes an optical sensing module, and an optical sensor of the optical sensing module generates an analog signal with a skin characteristic signal and a vessel characteristic signal according to an optical reflecting signal. The skin characteristic signal corresponds to a skin feature of an user, and the vessel characteristic signal corresponds to a vessel feature of the user. The signal generating circuit is electrically connected to the analog processing circuit and adapted to transform the analog signal into a compensation signal. The DC voltage detecting circuit is electrically connected to the signal generating circuit and adapted to compensate the analog processing circuit according to the compensation signal, so as to decrease the skin characteristic signal within the analog signal.

According to the claimed invention, the optical sensing module further includes a switch electrically connected between the optical sensor and the signal generating circuit. The DC voltage detecting circuit controls signal quantity through the switch by varying gate voltage of the switch so as to compensate the analog processing circuit.

According to the claimed invention, the optical sensing module further includes a switch and a charge capacity. The switch is electrically connected between the charge capacity, the optical sensor and the signal generating circuit. The DC voltage detecting circuit controls charging level of the charge capacity by varying gate voltage of the switch, so as to compensate the analog processing circuit.

According to the claimed invention, the optical sensing module further includes a gain module electrically connected between the optical sensing module and the signal generating circuit. The DC voltage detecting circuit controls gain result of the gain module applied to the analog signal by varying a compensating voltage value of a compensation capacity of the gain module, so as to compensate the analog processing circuit.

According to the claimed invention, the switch is an N-type Metal oxide semiconductor field effect transistor, a P-type Metal oxide semiconductor field effect transistor or a transmission gate.

The vessel sensing device of the present invention can automatically deduct the redundant voltage resulted by the skin characteristic signal to accordingly increase the ratio of the vessel characteristic signal to the analog signal through the output port of the analog processing circuit while detecting the skin texture with different colors. The present invention utilizes the DC voltage detecting circuit to dynamically amend the analog processing circuit, the analog processing circuit outputs the analog signal wherefrom the skin characteristic signal is deducted, quantity of the analog signal can be enormously condensed to reduce calculation and transformation demands of electronic components of the vessel sensing device, and the vessel sensing device can have advantages of low power consumption, small-size mode and excellent sensory precision.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
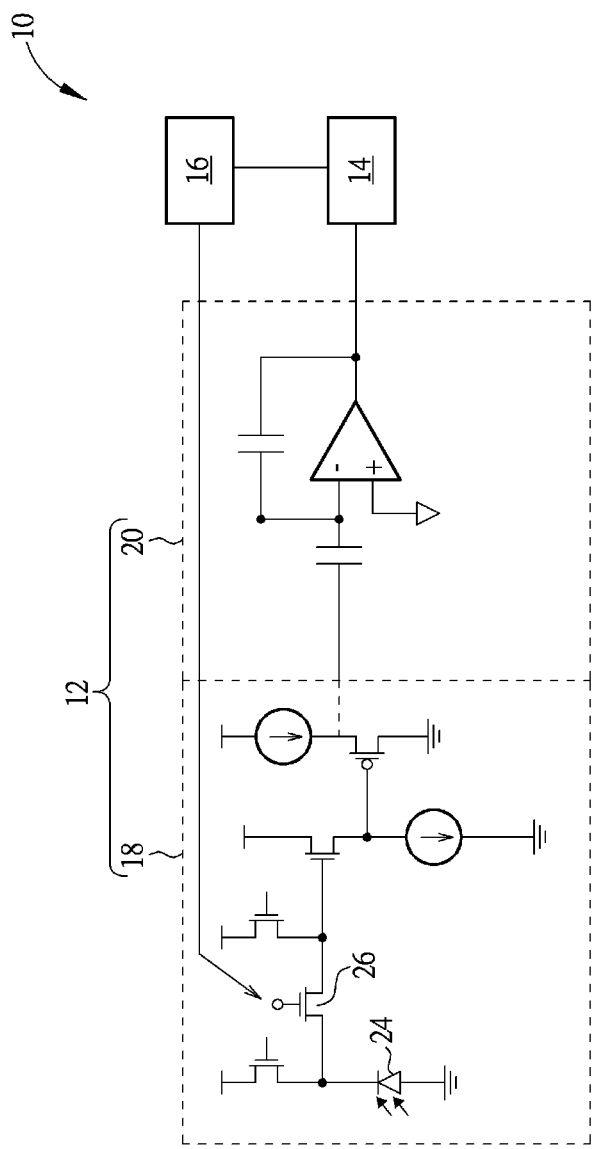
FIG. 1 is a diagram of a vessel sensing device according to a first embodiment of the present invention.

Please refer to FIG. 1. FIG. 1 is a diagram of a vessel sensing device 10 according to a first embodiment of the present invention. The vessel sensing device 10 includes an analog processing circuit 12, a signal generating circuit 14 and a direct current (DC) voltage detecting circuit 16. The vessel sensing device 10 is usually applied to the smart phone, the smart watch and any wearable device. The vessel sensing device 10 utilizes the analog processing circuit 12 to detect surface texture of the user so as to accordingly generate an analog signal by noninvasive optical sensing technology, and the analog signal contains a skin characteristic signal of the skin surface layer and a vessel characteristic signal of the skin sublayer. The skin characteristic signal corresponds to skin features of the user, such as skin color and/or roughness. The vessel characteristic signal corresponds to vessel features of the user, such as contractive variation of the vessel. That is, the skin characteristic signal within the analog signal is redundant noise for the vessel sensing device 10.

Different users provide different skin characteristic signal according to diversity of races and/or habits. For instance, a ratio of the skin characteristic signal of tanned skin to the analog signal is greater than a ratio of the skin characteristic signal of lightly pigmented skin to the analog signal. As the ratio of the skin characteristic signal to the analog signal obtained by the analog processing circuit 12 is greater than a threshold, the vessel sensing device 10 is difficult to recognize the vessel characteristic signal from the skin characteristic signal, and cannot provide proper heart rhythm information, sentiment index and/or pressure index for reference. Therefore, the vessel sensing device 10 utilizes the signal generating circuit 14 to transform the analog signal of the analog processing circuit 12 into a compensation signal. The DC voltage detecting circuit 16 can dynamically compensate the analog processing circuit 12 according to the compensation signal while being applied to the surface texture with different skin color, so as to reduce the skin characteristic signal within the analog signal to accordingly decrease interference of the vessel detecting result which may be affected by the skin color and/or roughness.

In the first embodiment, the analog processing circuit 12 includes an optical sensing module 18 and a gain module 20. The optical sensing module 18 receives an optical signal reflected from the skin to detect contraction of the vessel and to generate the corresponding analog signal by the noninvasive optical sensing technology, such as the photoplethysmogram technology. For example, the optical sensing module 18 includes an optical sensor 24. A wavelength range of the optical signal conforms to a detective range of the optical sensor 24. The optical signal preferably can be an invisible optical signal to prevent noise interference of environmental background. The optical signal is projected onto the surface texture of the user, and the optical sensor 24 can generate a photosensitive signal according to the optical reflecting signal formed by the optical signal reflected from the surface texture. The photosensitive signal contains parameters corresponding to the skin characteristic signal and the vessel characteristic signal of the skin texture.

The gain module 20 is electrically connected between the optical sensing module 18 and the signal generating circuit 14 to enlarge the photosensitive signal detected by the optical sensing module 18, and the corresponding analog signal is generated through an output port of the analog processing circuit 12. The signal generating circuit 14 is electrically connected between the analog processing circuit 12 and the DC voltage detecting circuit 16, to transform the analog signal from the analog processing circuit 12 into the compensation signal for the DC voltage detecting circuit 16. The signal generating circuit 14 can be the analog to digital (A/D) converter which transforms the analog signal into the digital compensation signal. In order to decrease interference of the skin characteristic signal with the vessel detecting result, the optical sensing module 18 of the first embodiment includes a first switch 26 electrically connected between the optical sensor 24 and the signal generating circuit 14. The vessel sensing device 10 utilizes the DC voltage detecting circuit 16 to dynamically compensate the gate voltage of the first switch 26, so as to control photosensitive signal quantity through the first switch 26 by varying the gate voltage. For example, the DC voltage detecting circuit 16 can reduce the gate voltage of the first switch 26, quantity of the photosensitive signal through the first switch 26 is decreased to accordingly deduct the direct current (DC) voltage value from the skin characteristic signal or to decrease a ratio of the DC voltage value to the skin characteristic signal. The vessel characteristic signal within the analog signal output by the analog processing circuit 12 can be fully reserved.

Figure 2:
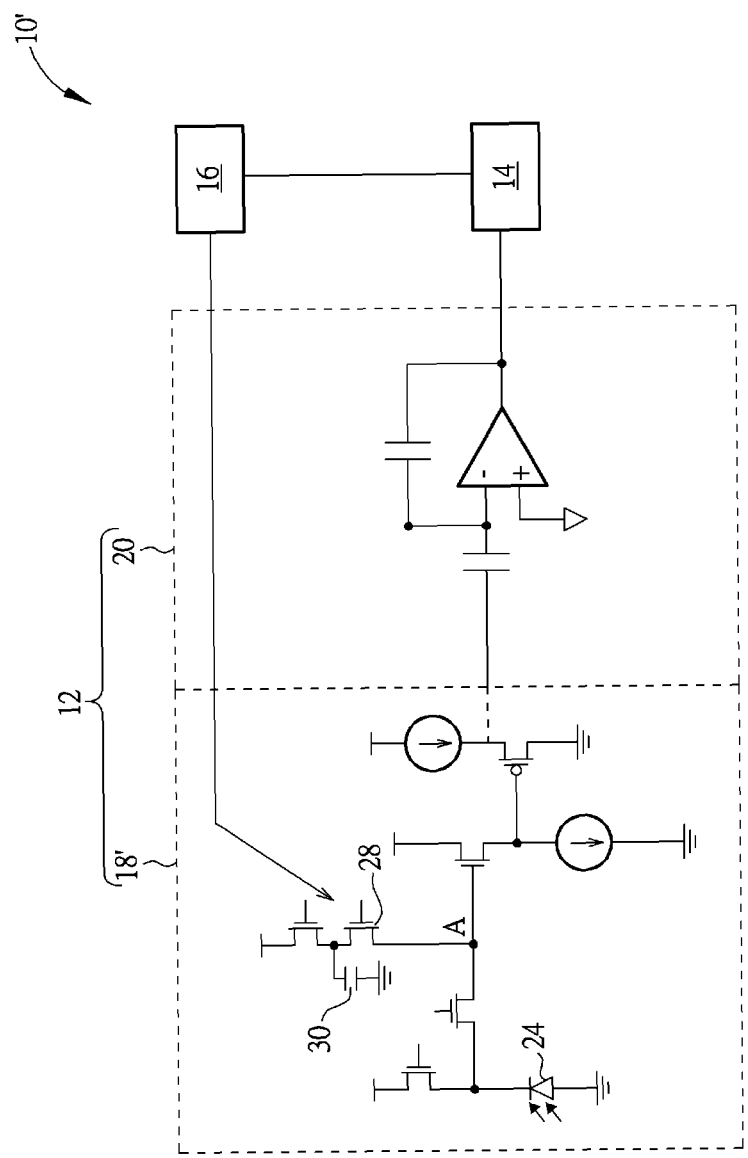
FIG. 2 is a diagram of the vessel sensing device according to a second embodiment of the present invention.

Please refer to FIG. 2. FIG. 2 is a diagram of the vessel sensing device 10' according to a second embodiment of the present invention. In the second embodiment, elements having the same numeral as ones of the first embodiment have the same structures and functions, and a detailed description is omitted herein for simplicity. The optical sensing module 18' of the vessel sensing device 10' further includes a second switch 28 and a charge capacity 30. The second switch 28 is electrically connected between the charge capacity 30, the optical sensor 24 and the signal generating circuit 14. The DC voltage detecting circuit 16 controls charging level of the charge capacity 30 by varying the gate voltage of the second switch 28 to dynamically compensate the analog processing circuit 12. That is, the DC voltage detecting circuit 16 can activate the second switch 28 to charge the charge capacity 30. Parts of the photosensitive signal may flow toward the charge capacity 30 via the second switch 28 while passing through the node A, which means the DC voltage value of the photosensitive signal corresponding to the skin characteristic signal can be deducted (or the ratio of the DC voltage value to the photosensitive signal can be decreased). Deduction of the DC voltage value from the photosensitive signal becomes greater since activating level of the second switch 28 becomes larger, and the analog signal through the output port of the analog processing circuit 12 can fully reserve the important vessel characteristic signal.

Figure 3:
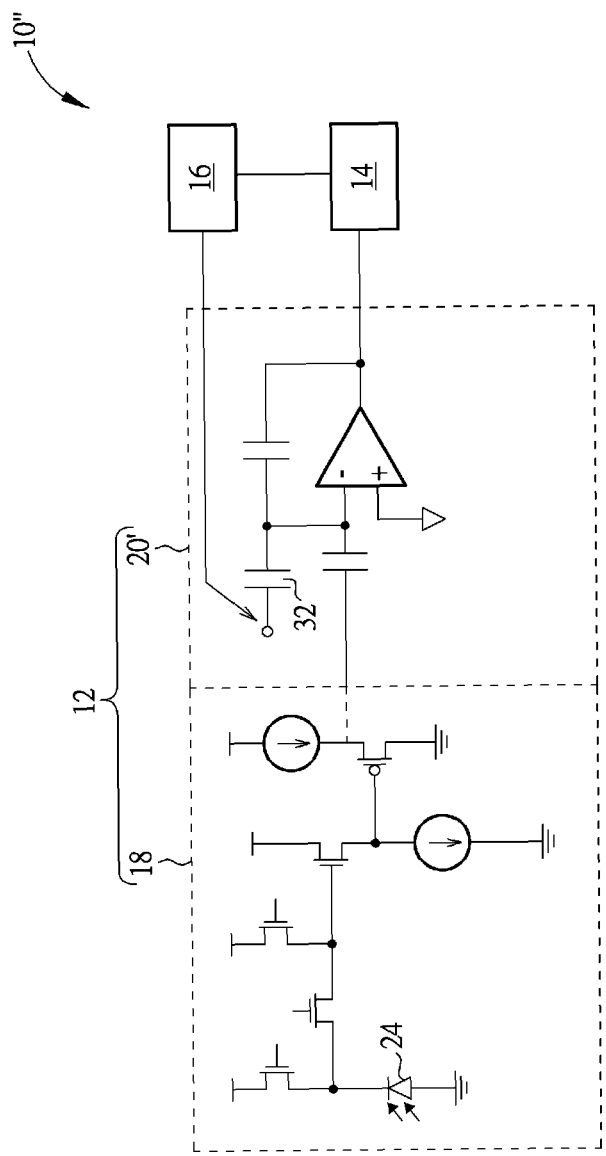
FIG. 3 is a diagram of the vessel sensing device according to a third embodiment of the present invention.

Please refer to FIG. 3. FIG. 3 is a diagram of the vessel sensing device 10" according to a third embodiment of the present invention. In the third embodiment, elements having the same numerals as ones of the above-mentioned embodiments have the same structures and functions, and the detailed description is omitted herein for simplicity. The optical sensing module 18 of the vessel sensing device 10" includes the optical sensor 24 which is grounded. The gain module 20' enlarges the vessel characteristic signal and the skin characteristic signal of the analog signal simultaneously. In order to reduce the redundant skin characteristic signal within the analog signal, the gain module 20' of the third embodiment includes a compensation capacity 32, and the vessel sensing device 10" utilizes the DC voltage detecting circuit 16 to adjust a compensating voltage value of the compensation capacity 32, so as to control gain result of the gain module 20' relative to the analog signal. During gain process of the analog signal, the skin characteristic signal is deducted by the compensation capacity 32 although the gain result of the skin characteristic signal and the vessel characteristic signal are similar, so the vessel sensing device 10" can effectively prevent the vessel detecting result from being interfered by the skin characteristic signal by varying the gain result of the analog signal.

In conclusion, the vessel sensing device of the present invention can automatically deduct the redundant voltage resulted by the skin characteristic signal to accordingly increase the ratio of the vessel characteristic signal to the analog signal through the output port of the analog processing circuit while detecting the skin texture with different colors. The DC voltage detecting circuit of the first embodiment utilizes the first switch electrically connected to the optical sensor to constrain the signal quantity through the first switch, so as to deduct the DC voltage value (which corresponds to the skin characteristic signal) from the photosensitive signal generated by the optical sensor. The DC voltage detecting circuit of the second embodiment utilizes the second switch electrically connected to the charge capacity to determine charge capacity of the charge capacity by adjusting the activating level of the second switch, so a to accordingly deduct the specific DC voltage value. The switches of the first embodiment and the second embodiment can be the N-type Metal oxide semiconductor field effect transistor (MOSFET), the P-type Metal oxide semiconductor field effect transistor (MOSFET) or the transmission gate. The DC voltage detecting circuit of the third embodiment controls the gain result of the gain module to deduct or decrease the skin characteristic signal within the analog signal.

Therefore, the present invention utilizes the DC voltage detecting circuit to dynamically amend the analog processing circuit, the analog processing circuit outputs the analog signal wherefrom the skin characteristic signal is deducted, quantity of the analog signal can be enormously condensed to reduce calculation and transformation demands of electronic components of the vessel sensing device, and the vessel sensing device can have advantages of low power consumption, small-size mode and excellent sensory precision.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A vessel sensing device with automatic amendment function, comprising
    an analog processing circuit, the analog processing circuit comprising an optical sensing module, an optical sensor of the optical sensing module generating an analog signal with a skin characteristic signal and a vessel characteristic signal according to an optical reflecting signal, wherein the skin characteristic signal corresponds to a skin feature of an user, and the vessel characteristic signal corresponds to a vessel feature of the user, the optical sensing module further comprising a switch electrically connected to the optical sensor;
    a signal generating circuit electrically connected to the analog processing circuit and the switch and adapted to transform the analog signal into a compensation signal; and
    a direct current (DC) voltage detecting circuit electrically connected to the signal generating circuit and adapted to compensate the analog processing circuit according to the compensation signal, so as to decrease the skin characteristic signal within the analog signal, the DC voltage detecting circuit controlling signal quantity through the switch by varying gate voltage of the switch so as to compensate the analog processing circuit.

2. The vessel sensing device of claim 1, wherein the DC voltage detecting circuit reduces the gate voltage to deduct a DC voltage value, so as to decrease the skin characteristic signal within the analog signal.

3. The vessel sensing device of claim 1, wherein the optical sensing module further comprises a gain module electrically connected between the optical sensing module and the signal generating circuit, the DC voltage detecting circuit controls gain result of the gain module applied to the analog signal by varying a compensating voltage value of a compensation capacity of the gain module, so as to compensate the analog processing circuit.

4. The vessel sensing device of claim 3, wherein the DC voltage detecting circuit utilizes the compensation capacity to reduce the gain result of the gain module applied to the analog signal, so as to decrease the skin characteristic signal within the analog signal.

5. The vessel sensing device of claim 1, wherein the switch is an N-type Metal oxide semiconductor field effect transistor, a P-type Metal oxide semiconductor field effect transistor or a transmission gate.

6. A vessel sensing device with automatic amendment function, comprising
    an analog processing circuit, the analog processing circuit comprising an optical sensing module, an optical sensor of the optical sensing module generating an analog signal with a skin characteristic signal and a vessel characteristic signal according to an optical reflecting signal, wherein the skin characteristic signal corresponds to a skin feature of an user, and the vessel characteristic signal corresponds to a vessel feature of the user, the optical sensing module further comprising a switch and a charge capacity;
    a signal generating circuit electrically connected to the analog processing circuit and adapted to transform the analog signal into a compensation signal, the switch being electrically connected between the charge capacity, the optical sensor and the signal generating circuit; and
    a direct current (DC) voltage detecting circuit electrically connected to the signal generating circuit and adapted to compensate the analog processing circuit according to the compensation signal, so as to decrease the skin characteristic signal within the analog signal, the DC voltage detecting circuit controlling charging level of the charge capacity by varying gate voltage of the switch so as to compensate the analog processing circuit.

7. The vessel sensing device of claim 6, wherein the DC voltage detecting circuit activates the switch to charge the charge capacity, so as to deduct a DC voltage value to accordingly decrease the skin characteristic signal within the analog signal.

8. The vessel sensing device of claim 6, wherein the switch is an N-type Metal oxide semiconductor field effect transistor, a P-type Metal oxide semiconductor field effect transistor or a transmission gate.

9. The vessel sensing device of claim 6, wherein the optical sensing module further comprises a gain module electrically connected between the optical sensing module and the signal generating circuit, the DC voltage detecting circuit controls gain result of the gain module applied to the analog signal by varying a compensating voltage value of a compensation capacity of the gain module, so as to compensate the analog processing circuit.

10. The vessel sensing device of claim 9, wherein the DC voltage detecting circuit utilizes the compensation capacity to reduce the gain result of the gain module applied to the analog signal, so as to decrease the skin characteristic signal within the analog signal.

* * * * *